United States Patent [19]

Noda

[11] Patent Number: 4,517,309

[45] Date of Patent: May 14, 1985

[54] METHOD FOR THE TREATMENT OF CALCIFYING PANCREATITIS

[76] Inventor: Aiji Noda, 204-402, No. 2-3, Fujiyamadai 2-chome, Kasugai-shi, Aichi-ken, Japan

[21] Appl. No.: 575,897

[22] Filed: Feb. 1, 1984

[30] Foreign Application Priority Data

Apr. 6, 1983 [JP] Japan ................................. 58-61666

[51] Int. Cl.³ ............................................ A61K 31/42
[52] U.S. Cl. .................................................... 514/376
[58] Field of Search ........................................ 424/272

[56] References Cited

U.S. PATENT DOCUMENTS 3,709,895  1/1973  Kohlhaupt et al. ................. 424/272
4,183,960  1/1980  Asher et al. ......................... 424/358
4,367,234  1/1983  Schnur ............................... 424/272

OTHER PUBLICATIONS

Konishi et al., "Experimental Pancreatolithiasis in the Dog", Surgery 89(6):687-691, (1981).

A. Noda et al., "Trimethadione (Troxidone) Dissolves Pancreatic Stones", The Lancet, 1984, 351-353.

Chem. Abstracts, 90(23):179861q, (1979).

Noda et al., "Pancreatolithiasis and Pancreatic Carcinoma", Arch. Intern. Med., vol. 137, 754-760, Jun. 1977.

Noda et al., "Clinical Evaluation of Pancreatic Excretion Test with Dimethadione and Oral BT-PABA Test in Chronic Pancreatis", Digestive Diseases and Sciences, vol. 28, 230-235, Mar. 1983.

Sarles et al, "Treatment of Chronic Calcifying Pancreatitis by Oral Long-Term Administration of Citrate. Preliminary Results", Gastroenterol. Clin. Biol. (Paris) 3, 615-620, (1979).

Primary Examiner—Albert T. Meyers
Assistant Examiner—Joyce L. Morrison
Attorney, Agent, or Firm—Wegner & Bretschneider

[57] ABSTRACT

Method for the treatment of calcifying pancreatitis which comprises administering an effective amount of trimethadione or dimethadione to a patient suffering from calcifying pancreatitis, by which pancreatic stones are effectively dissolved out.

5 Claims, No Drawings

METHOD FOR THE TREATMENT OF CALCIFYING PANCREATITIS

The present invention relates to a method for the treatment of calcifying pancreatitis. More particularly, it relates to a method for the treatment of calcifying pancreatitis comprising administering an effective amount of trimethadione (i.e. 3,5,5-trimethyloxazolidine-2,4-dione) or dimethadione (i.e. 5,5-dimethyloxazolidine-2,4-dione) to patients suffering from calcifying pancreatitis.

Trimethadione is widely used as a medicine for the treatment of petit mal patients. Besides, it is well known that when trimethadione is orally administered to humans, it is metabolized within the body to be converted into dimethadione which is excreted in pancreatic juice in a high concentration. By utilizing this property, trimethadione is used for early diagnosis of chronic pancreatitis (cf. Arch. Intern. Med., Vol. 137, 754–760, June, 1977, and Digestive Diseases and Sciences, Vol. 28, 230–235, March, 1983)

Calcifying pancreatitis is usually initiated by formation of protein plugs within the pancreatic ducts, followed by precipitation of calcium carbonate (pancreatic stones). The stones are usually produced during the course of chronic pancreatitis, particularly alcoholic chronic pancreatitis, and advance inflammation of the gland, which results in gradual and irreversible lowering of the pancreatic endocrine and exocrine functions. Moreover, they frequently cause abdominal colicky pain and occasionally induce various complications including pancreatic cyst, abscess, and diabetes, for which surgical interventions and insuline therapy are inevitably required.

Such a vicious circle as mentioned above can be stopped by removing the pancreatic stone at an earlier stage of its formation.

In alcoholic calcifying pancreatitis, the stone is relatively small, usually less than 5 mm in diameter on abdominal plain X-ray film. In idiopathic or hereditary calcifying pancreatitis, on the other hand, the stone is generally a larger one. In both types of calcifying pancreatitis, distribution of the stone in the gland is diffused in more than half of the patients.

So far there have been several trials to remove the pancreatic stone in patients suffering from recurrent abdominal pain or some complications. One is the surgical removal of the stone by exposing the pancreatic duct, followed by pancreatojejunostomy. Others are the endoscopic removal of the stone. Recently, some clinicians have tried to remove the pancreatic stone in the main pancreatic duct near the Vater's papilla by using a basket catheter to catch the stone after the endoscopic papillotomy. Another is the method for frequent washing out of protein plugs under secretin stimulation through a catheter inserted into the main pancreatic duct via the Vater's papilla.

All these methods, however, give a lot of mental, physical and economical stress to the patients and do not seem so effective for the removal of the pancreatic stone. Hence, their indication is restricted to a particular type of calcifying pancreatitis.

A medical removal of the pancreatic stone has been tried only by Sarles et al in France (cf. Sarles, H., et al., Gastroenterol. Clin. Biol., (Paris) 3, 615 –620, 1979). This is the method of oral administration of citric acid and its salt to patients with calcifying pancreatitis. There is, however, no further report of this stone dissolution. In this method, a dose of citric acid and its salt is so large (10.6 g a day) that undesirable side effects, such as diarrhea, has been reported. Therefore, it seems unlikely that this method will become a useful tool for the pancreatic stone dissolution. Development of a new drug is strongly desired for the medical removal of the pancreatic stone.

Under the circumstance, the present inventor has studied an improved medicine for the treatment of calcifying pancreatitis. As a result, it has been found that trimethadione and dimethadione are useful for pancreatic stone dissolution, that is the treatment of calcifying pancreatitis.

An object of the present invention is to provide a new method for the treatment of calcifying pancreatitis. This and other objects and advantages of the present invention are apparent to persons skilled in the art from the following description.

According to the present invention, calcifying pancreatitis is treated by giving an effective amount of trimethadione or dimethadione to patients with calcifying pancreatitis.

Trimethadione used in the present invention may be a product commercially available in the form of a sugar coated tablet or powder, or may be obtained by preparing a bulk material of trimethadione by a known method, followed by preparing into a conventional pharmaceutical preparation suitable for oral administration, such as tablets, capsules, powders, granules, or fine granules in admixture with a conventional carrier or diluent. The preparations contain trimethadione in an amount of 100 to 1,000 mg per dosage unit. Besides, dimethadione can be prepared by a known method, followed by preparing into a conventional pharmaceutical preparation suitable for oral or parenteral administration, such as tablets, capsules, powders, granules, fine granules, solutions, emulsions, suspensions, or the like in admixture with a conventional carrier or diluent.

Trimethadione is preferably administered by the oral route in a dose of 0.5 to 3 g/day, preferably 1 to 2 g/day, which may be divided into two to four times per day. Dimethadione is preferably administered by the intravenous route so that it maintains a blood level of about 0.5 mg/ml, i.e. in a dose of 10 to 300 mg/kg/day. The administration of the medicine is preferably continued for a long period of time, at least for one month, usually for one to three months, because it is not effective when administered orally for a few days. According to the symptom, it is continued for longer period of time.

When trimethadione is administered, it does not show the pancreatic stone-dissolving activity as it stands, but it shows the desired activity after being absorbed in the body. That is, it is assumed that when trimethadione is orally administered and absorbed, it is de-methylated to be converted into dimethadione, and the dimethadione is excreted into pancreatic juice from blood in a high concentration and then exhibits the pancreatic stone-dissolving activity.

The activity of the present medicine is illustrated by the following experiments.

EXPERIMENT 1

(in vitro test)

Preparation of test solution:

To 1/20 M aqueous NaHCO$_3$ solution (pH 8.31) was added dimethadione in various amounts to prepare aqueous solutions of dimethadione having various concentrations, such as 0.05% solution (pH 7.62), 0.1% solution (pH 7.29), 0.2% solution (pH 6.97), 0.5% solution ( pH 6.56), and 1% solution (pH 6.28).

Method:

Each aqueous solution (100 ml) obtained above was added to a flask, and thereto was added pancreatic stones obtained surgically from human, and the flask was sealed and kept at 37° C. Once a week, the solution was exchanged with a fresh one, and each time or every other week, the stones were dried and weighed.

Result:

The pancreatic stones were completely dissolved and disappeared after 5 weeks in case of 1% solution (weight of the stone: 24.5 mg), after 11 weeks in case of 0.5% solution (weight of the stone: 21.2 mg), and after 58 weeks in case of 0.2% solution (weight of the stone: 22.6 mg).

In case of 0.1% and 0.05% solutions, the stones were gradually decreased, and after 96 weeks, 33.1 mg of stones were removed (total weight of the stone: 48.0 mg) in case of the former, and 40.1 mg were removed in case of the latter (total weight of the stone: 169.2 mg).

In reference wherein 1/20 M aqueous NaHCO$_3$ solution was used, even after 96 weeks, the stones were decreased merely in an amount of 3 mg (total weight of the stone: 13 mg).

EXPERIMENT 2

(in vivo test)

Production of experimental calcifying pancreatitis:

Calcifying pancreatitis was produced in dogs in accordance with the method by Konishi et al. (cf. Surgery, Vol. 89, 687–691, June, 1981). Each dog was anesthetized with laughing gas (dinitrogen oxide gas) and halothane (i.e. 2-bromo-2-chloro-1,1,1-trifluoroethane) and then the abdomen was opened. The major pancreatic duct was triple ligated at the pancreatoduodenal junction, while the minor pancreatic duct remained opened. Round markers with a stainless steel fine wire were set around the duodenal junction of both pancreatic ducts. Besides, a Thomas gastric cannula was prepared on the anterior wall of the fundus and then taken out through the left flank. Four days after the operation, feeding with a solid feed was started again.

Abdominal X-ray photography:

From 3 months after the operation, abdominal plain X-ray photography films were taken. After about 24 hours fast, the dog was anesthetized with ketamine hydrochloride (i.e. 2-(o-chlorophenyl)-2-(methylamino)cyclohexanone hydrochloride) and pentobarbital sodium. Through the gastric cannula, the stomach was cleaned up, and then air (about 200 ml) was sent through a Nelaton catheter provided with a cork stopper. X-rays were taken at 55–58 KVP, 100–200 mA, and 0.05–0.1 second exposure with Fuji G-4 sentitized paper and Fuji RXO film (grid, 5 : 1). In each dog, eight X-ray films were taken in one experiment on antero-posterior (en face) right and left oblique positions.

Experiment of dissolving pancreatic stones:

When shadow of calcification was observed on the films obtained, the photography was continued for additional one or two months in order to confirm an increase and/or an enlargement in the calcification shadow, and thereafter, trimethadione was administered. Both two markers were set at the pancreatoduodenal junctions and gastric aerogram were useful to assume the portion of the calcification shadow. Trimethadione was orally administered together with a solid feed in the form of a sugar tablet in a dose of 1,000–1,500 mg/day, dividing into twice per day.

After X-ray photography was finished, venous blood was taken in each experiment for measurement of various factors such as blood cells, liver function, lipids, electrolytes (Na, K, Cl, Ca), blood sugar, amylase and total bililubin. In dogs to which trimethadione was administered, plasma concentration of dimethadione was also determined.

Results:

Test 1: male dog (body weight: 13.8 kg)

Three months after the operation, there were observed multiple small calcification shadows on both sides of the marker provided around the major pancreatic duct. The shadows tended to move upper or lower. After one month (4 months after the operation), the calcification was enlarged, and hence, on the next day after X-ray examination, oral administration of trimethadione in a dose of 1,000 mg/day was begun. Two months after the administration of trimethadione (6 months after the operation), the calcification shadow completely disappeared on the X-ray photograms (hereinafter, it is abbreviated as "XP"). At that time, plasma concentration of dimethadione was 414 µg/ml. Two months after cessation of trimethadione (8 months after the operation), clear calcification shadow appeared again at the cephalic side of the marker provided around the major pancreatic duct (that is, at the upper part on the XP). After an additional one month (9 months after the operation), the shadow became much clearer, and a small calcification shadow further appeared at the distal part of the marker (i.e. at the lower part on the XP). Hence, trimethadione was again administered in a dose of 1,200 mg/day. One month after re-administration of trimethadione (10 months after the operation), the small shadow at the distal part of the marker was observed no more, but the main shadow was not changed at all in shape (at this time, plasma concentration of dimethadione was 400 µg/ml). The dose of trimethadione was then increased up to 1,500 mg/day. After one month (11 months after the operation), a round-shape image translucent to the X-rays appeared within the shadow, the size was shortened in lengthwise direction (7 mm→5 mm) and the top part became more sharp. The dose of trimethadione was maintained as above (at this time, plasma concentration of dimethadione was 400 µg/ml). After an additional one month (12 months after the operation), the shadow completely disappeared again on the XP (at this time, plasma concentration of dimethadione was 421 µg/ml). No abnormal finding was observed in blood examinations. The body weight of the animal was increased from 13.8 to 17.3 kg.

Test 2: male dog (body weight: 12 kg)

Nine months after the operation, a few small calcification shadows appeared at the right lobe of the pancreas on the XP. After one month (10 months after the operation), the shadows became larger and much clearer, and two small round shadows further appeared in the left lobe of the gland. One month after administration of trimethadione in a dose of 1,200 mg/day (11 months after the operation), these shadows completely disappeared on the XP (at this time, plasma concentration of dimethadione was 539 µg/ml). Even 6 months after cessation of the dose (17 months after the operation), no clear calcification shadow was observed on the XP. No abnormal finding was observed in blood examinations. The body weight of the animal was increased from 12 to 15.2 kg.

Test 3: male dog (body weight: 12.6 kg)

Six months after the operation, fairly clear calcification shadows appeared around both markers and also at the left lobe of the pancreas on the XP. After one month (7 months after the operation), the shadows by the marker provided around the major pancreatic duct were enlarged, and multiple small shadows were further observed in the left lobe of the gland. On the next day of the X-ray examination, the administration of trimethadione started in a dose of 1,000 mg/day. After one month (8 months after the operation), the shadows became wholly light. As plasma concentration of dimethadione was low as 378 μg/ml, the dose of trimethadione was increased up to 1,200 mg/day. After one month (9 months after the operation), the shadows showed the linear arrangement like ranged coins and had fine projections on their circumference (at this time, plasma concentration of dimethadione was 579 μg/ml). After an additional one month (10 months after the operation), the shadow like ranged coins was split into three parts, and the largest one by the marker around the major pancreatic duct became smaller (at this time, plasma concentration of dimethadione was 361 μg/ml). After an additional one month (11 months after the operation), the shadows became extremely light, and there was observed a new image by the marker around the major pancreatic duct, which was considered to be an inner shadow of the major duct responsible for calcium in the juice dissolved out from stones (at this time, plasma concentration of dimethadione was 485 μg/ml). No abnormal finding was observed in blood examinations. The body weight of the animal was increased from 12.6 to 14.2 kg.

Test 4: (reference experiment)

(a) Male dog (body weight: 12 kg)

In this case, no trimethadione was administered, while calcification shadows were observed.

Three and a half months after the operation, clear rectangular calcification shadow was observed at the cephalic part of the markers provided around the major pancreatic duct. After one month (4.5 months after the operation), the shadow became clearer and downward (at the distal side) concaved shadow. After additional one month (5.5 months after the operation), the shadow was much enlarged (4×8 mm), and a few irregular translucent images were also observed within it. After additional one month (6.5 months after the operation), a new calcification shadow (2×3 mm) appeared at the right lobe of the pancreas. The body weight of the animal was increased from 12 to 14.6 kg.

(b) Male dog (body weight: 14.3 kg)

In this case, two markers were set around both pancreatic ducts without ligation of the major pancreatic duct in order to detect possiblity of both spontaneous production of the pancreatic stone and appearance of a pseudo-positive shadow (i.e. shadow resulting from factors other than the pancreatic stone) due to the operation.

Fourteen months after the operation, no calcification shadow was observed.

EXPERIMENT 3

(Clinical test)

The patient was a 57-year old male with alcoholic chronic calcifying pancreatitis. The pancreatic stone was first found at 50 years old. Between 53 to 55 years old, he was admitted into a hospital because of recurrent severe abdominal pain after alcohol ingestion. The pancreatic stone was localized in the head of the pancreas at 53 years old, but was wholly expanded when he was readmitted into a hospital. The endoscopic retrograde pancreatography demonstrated irregular dilatation of the main pancreatic duct and its branches, and calculi in varying sizes in the ducts.

With well informed consent from the patient, trimethadione was orally given in a dose of 1,200–1,500 mg/day, which was divided into three times in a day. The change of the pancreatic stone was followed by both abdominal plain X-ray photography and computed axial tomography. After 10 months, the calcification in the tail of the pancreas was decreased in size and number, and after 18 months, it almost disappeared. However, the calcification in the head of the pancreas remained still. During the course of the test, plasma concentration of dimethadione ranged from 401 to 610 μg/ml and there was observed no abdominal finding resulting from the medication. However, since the patient complained of photophobia, the dose of the medicine was inevitably decreased from 1,500 mg/day to 1,200 mg/day.

What is claimed is:

1. A method for the treatment of calcifying pancreatitis which comprises orally administering trimethadione in a dose of 0.5 to 3 g/day at least for one month to a patient suffering from calcifying pancreatitis to thereby dissolve pancreatic stones.

2. A method according to claim 1, wherein trimethadione is administered in a dose of 1 to 2 g/day for one to three months.

3. A method according to claim 1, wherein trimethadione is used in the form of a preparation containing 100 to 1000 mg of trimethadione in admixture with a pharmaceutically acceptable carrier.

4. A method for the treatment of calcifying pancreatitis which comprises intravenously administering dimethadione in a dose of 10 to 300 mg/kg/day at least for one month to a patient suffering from calcifying pancreatitis to thereby dissolve pancreatic stones.

5. A method for the treatment of calcifying pancreatitis comprising
administering for at least one month trimethadione or dimethadione in a quantity sufficient to dissolve pancreatic stones to a patient suffering from pancreatitis.

* * * * *